(12) United States Patent
Froehlich et al.

(10) Patent No.: US 9,790,546 B2
(45) Date of Patent: Oct. 17, 2017

(54) MICROFLUIDIC CHIP, DEVICE AND SYSTEM FOR THE GENERATION OF AQUEOUS DROPLETS IN EMULSION OIL FOR NUCLEIC ACID AMPLIFICATION

(71) Applicant: Roche Molecular Systems, Inc., Pleasanton, CA (US)

(72) Inventors: Thomas Froehlich, Penzberg (DE); Jens Bolle, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 348 days.

(21) Appl. No.: 14/016,840

(22) Filed: Sep. 3, 2013

(65) Prior Publication Data

US 2014/0065631 A1     Mar. 6, 2014

Related U.S. Application Data

(60) Provisional application No. 61/695,913, filed on Aug. 31, 2012.

(51) Int. Cl.

| B01L 7/00 | (2006.01) |
|---|---|
| B01F 5/04 | (2006.01) |
| B01F 13/00 | (2006.01) |
| B01F 3/08 | (2006.01) |
| B01L 3/02 | (2006.01) |
| B01L 3/00 | (2006.01) |
| C12Q 1/68 | (2006.01) |

(52) U.S. Cl.
CPC ............ *C12Q 1/686* (2013.01); *B01F 3/0807* (2013.01); *B01F 5/0478* (2013.01); *B01F 13/0059* (2013.01); *B01L 3/0293* (2013.01); *B01L 3/502784* (2013.01); *B01L 3/0241* (2013.01); *B01L 7/52* (2013.01); *B01L 2200/0673* (2013.01); *B01L 2400/0487* (2013.01)

(58) Field of Classification Search
None
See application file for complete search history.

(56) References Cited

U.S. PATENT DOCUMENTS

| 6,281,254 B1 | 8/2001 | Nakajima et al. |
| 2004/0068019 A1 | 4/2004 | Higuchi et al. |
| 2005/0202489 A1 | 9/2005 | Cho et al. |
| 2005/0227264 A1 | 10/2005 | Nobile et al. |
| 2008/0003142 A1 | 1/2008 | Link et al. |
| 2008/0057546 A1* | 3/2008 | Lexow .............. C12N 15/10 435/91.52 |
| 2010/0173394 A1* | 7/2010 | Colston ............ B01F 3/0807 435/287.2 |
| 2010/0184020 A1 | 7/2010 | Beer et al. |

FOREIGN PATENT DOCUMENTS

WO     0223163 A1     3/2002

* cited by examiner

*Primary Examiner* — Angela M Bertagna
(74) *Attorney, Agent, or Firm* — Pamela C. Ancona; M. Reza Savari (57) ABSTRACT

A microfluidic chip, device, system, the use thereof and method for the generation of aqueous droplets in emulsion oil for nucleic acid amplification.

12 Claims, 8 Drawing Sheets

MICROFLUIDIC CHIP, DEVICE AND SYSTEM FOR THE GENERATION OF AQUEOUS DROPLETS IN EMULSION OIL FOR NUCLEIC ACID AMPLIFICATION

CROSS-REFERENCES TO RELATED APPLICATIONS

This application claims priority to U.S. Provisional Application No. 61/695,913, filed on Aug. 31, 2012, the content of which is incorporated by reference herein in its entirety.

FIELD OF THE INVENTION

The present description refers to a microfluidic chip, device, system, the use thereof and a method for the generation of aqueous droplets in emulsion oil for nucleic acid amplification.

BACKGROUND OF THE INVENTION

In recent years, quantitative amplification, such as qPCR, is a fast growing field. One specific development in this field is the so called digital PCR (dPCR) which is used for the detection of sequence variants with a very high sensitivity. Using dPCR, one mutation out of up to $10^5$ individuals can be detected. Such sensitivity cannot be reached by any other quantitative amplification method.

Technical challenges using dPCR are mainly the generation of the aqueous droplets in a hydrophobic environment. The aqueous droplets are used as compartments in which at average one single nucleic acid molecule is amplified and detected. Thus a single sample is partitioned into thousands or millions of individual reaction chambers, each containing either one or no copies of the sequence of interest. By assessing the number of positive partitions in which the target sequence could be detected versus the number of negative partitions, an exact determination of the original number of copies of a DNA in the original sample is possible. The sensitivity, efficiency and resolution power of a digital PCR system depends mainly on the number of aqueous partitions which can be derived from a single aqueous sample and on the size distribution among individual aqueous droplets.

SUMMARY OF THE INVENTION

The present description is directed to a microfluidic chip for the generation of aqueous droplets for nucleic acid amplification, said microfluidic chip comprising a) a first reservoir for uptake of a hydrophobic liquid ending in at least one inlet or at least one inlet coming from an external reservoir of hydrophobic liquid, each inlet ending into a first microfluidic channel connecting the at least one first reservoir with a reaction vessel, b) at least one element comprising a second reservoir for uptake of a hydrophilic solution ending in a vertical inlet into a second microfluidic channel connecting the second reservoir with a first microfluidic channel, c) at least one T-junction between said first and second microfluidic channel, characterized in that the end of said second microfluidic channel is joined radial and horizontal to the first microfluidic channel.

The present description is further directed to a device for the generation of aqueous droplets for nucleic acid amplification, the device comprising a microfluidic chip as described above, first means for providing a flow within said first microfluidic channel and second means for providing a flow within said second microfluidic channel.

The present description also refers to a system for digital PCR, the system comprising a) a device as described herein, b) a thermocycler instrument, and c) a read-out instrument.

Furthermore, the present descriptions is directed to the use of the microfluidic chip, device or system as described herein for performing digital PCR.

The present description is directed to a method for the generation of aqueous droplets for nucleic acid amplification, the method comprising the steps of a) providing a hydrophobic liquid in a first reservoir, b) providing a hydrophilic solution in a second reservoir, c) generating a first continuous flow of said hydrophobic liquid from said first reservoir through at least one inlet, each inlet ending into a first microfluidic channel, wherein the first microfluidic channel enters into a reaction vessel, d) generating a second continuous flow of said hydrophilic solution from said second reservoir through a second microfluidic channel, wherein the end of said second microfluidic channel is joined to the first microfluidic channel by at least one T-junction, and e) adjusting said first continuous flow and said second contiguous flow such that aqueous droplets of said hydrophilic solution are generated within said first continuous flow of hydrophobic liquid.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIG. 2: The Figure shows a unit of the microfluidic chip. The unit comprises a first reservoir (101) ending in one inlet (102) connecting the first reservoir (101) with a first microfluidic channel (103). Said first microfluidic channel (103) connecting the first reservoir (101) with a reaction vessel (121). The unit further comprises an element (110) comprising a second reservoir (111) for uptake of a hydrophilic solution ending in a vertical inlet (112) being the opening into a second microfluidic channel (113). The connection between the first (103) and the second microfluidic channel (113) is designed as a T-junction (114).

FIG. 5: Shows another embodiment for the generation of a higher number of aqueous droplets in the hydrophobic liquid. In this case, four T-junctions are formed between four endings of the second microfluidic channel and the first microfluidic channel. The four T-junctions are located on the same side of the first microfluidic channel.

FIG. 6: The figure shows another embodiment for the generation of a higher number of aqueous droplets in the hydrophobic liquid. In this case also four of the T-junctions are formed between four endings of the second microfluidic channel and the first microfluidic channel. However in this case, two of the four T-junctions are located on one side of the first microfluidic channel and two of the four T-junctions are located on the other side of the first microfluidic channel.

DETAILED DESCRIPTION OF THE INVENTION

By way of illustration, specific exemplary embodiments in which the invention may be practiced now are described.

The following definitions are set forth to illustrate and define the meaning and scope of various terms used herein.

The terms "a", "an" and "the" generally include plural referents, unless the context clearly indicates otherwise.

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification.

The term "microfluidic chip" refers to a substrate containing microfluidic structures, wherein volumes down to pico liters (pL) are handled within the microfluidic structures of the microfluidic chip. Microfluidic chips can be fabricated using lithography-based technologies, by molding, electroplating and milling.

The term "nucleic acid" generally refers to both DNA or RNA, whether it be a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3' or 5' overhangs and as such are not required or assumed to be completely double-stranded over their entire length. Furthermore, the term nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorphores and quenchers; phosphorothioate, methylphosphonates, phosphoroamidates and phosphorotiester linkages between nucleotides to prevent degradation; methylation; and modified bases such as deoxyInosine, 5-Bromo dU, deoxyUridine, 2-Aminopurine, dideoxyCytidine, 5-Methyl dC, locked nucleic acids (LNA's), Iso-dC and -dG bases, 2'-O-Methyl RNA bases and Fluorine Modified Bases.

The term "nucleotide" in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "operatively linked" is used herein to describe the connection between two or more individual instruments being part of the system according to the present description. Two or more individual instruments are "operatively linked" if they are arranged such that two or more methods are performed by the two or more individual instruments and said two or more methods appear as one single workflow. In addition a full integration of two or more individual instruments in a third integrated instrument is possible as well. Another possibility is to integrate different key features of the individual instruments mentioned above in a dedicated integrated device (e.g. a single microfluidic chip containing areas for microfluidic droplet generation, PCR amplification and droplet read-out).

The term "primer" refers to a polynucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include 32P, fluorescent dyes, electron-dense reagents, enzymes (as commonly used in ELISA assays), biotin, or haptens and proteins for which antisera or monoclonal antibodies are available.

The term "qPCR" generally refers to the PCR technique known as real-time quantitative polymerase chain reaction, quantitative polymerase chain reaction or kinetic polymerase chain reaction. This technique simultaneously amplifies and quantifies target nucleic acids using PCR wherein the quantification is by virtue of an intercalating fluorescent dye or sequence-specific probes which contain fluorescent reporter molecules that are only detectable once hybridized to a target nucleic acid.

As used herein, the term "sample" is used in its broadest sense. In one sense, it is meant to include a nucleic acid specimen obtained from any source. Biological nucleic acid samples may be obtained from animals (including humans) and encompass nucleic acids isolated from fluids, solids, tissues, etc. Biological nucleic acid sample may also come from non-human animals, including, but are not limited to, vertebrates such as rodents, non-human primates, ovines, bovines, ruminants, lagomorphs, porcines, caprines, equines, canines, felines, ayes, etc. Biological nucleic acids may also be obtained from prokaryotes, like bacteria and other non-animal eukaryotes such as plants. It is contemplated that the present description is not limited by the source of nucleic acids sample, and any nucleic acid from any biological Kingdom finds utility in methods as described herein.

The term "system" refers to two or more individual instruments which are operatively linked as defined above, such that the two or more individual instruments work as a unity. The methods performed by each individual instrument are connected with each other to form one single workflow performed by two or more individual instruments. In addition two or more individual instruments could be integrated in a third instrument resulting in a higher integrated system. Individual key elements of the tow or more individual instruments could be selected as well and integrated thereby forming a novel kind of individual instrument.

The present description refers to a microfluidic chip for the generation of aqueous droplets for nucleic acid amplification, said microfluidic chip comprising a) a first reservoir for uptake of a hydrophobic liquid ending in at least one inlet or at least one inlet coming from an external reservoir of hydrophobic liquid, each inlet ending into a first microfluidic channel connecting the at least one first reservoir with a reaction vessel, b) at least one element comprising a second reservoir for uptake of a hydrophilic solution ending in a vertical inlet into a second microfluidic channel connecting the second reservoir with a first microfluidic channel, c) at least one T-junction between said first and second microfluidic channel, characterized in that the end of said second microfluidic channel is joined radial and horizontal to the first microfluidic channel. In view of the connected first and second microfluidic channel, the term "horizontal" has to be construed such that the second microfluidic channel is connected to the first microfluidic channel within the level of the other first microfluidic channels within the microfluidic chip (See FIG. 3). Further, in view of the connected first and second microfluidic channel, the term "radial" has to be construed such that the second microfluidic channel is connected to the first microfluidic channel on a virtual line through the center of the first microfluidic channel.

In an embodiment, said end of the second channel is joined to the first channel in any possible angle. In a specific embodiment, said end of the second channel is joined to the first channel perpendicularly. The term "perpendicular" has to be construed such that the surface line of the second microfluidic channel is perpendicular to the surface line of the first microfluidic channel.

In one embodiment, one first reservoir ends in exactly one vertical inlet. In that case, the microfluidic chip comprises a first reservoir for uptake of a hydrophobic liquid for each first microfluidic channel as shown in FIG. 2. In a specific embodiment, said first reservoir for uptake of a hydrophobic liquid ends in at least one vertical inlet. In a more specific embodiment, said first reservoir for uptake of a hydrophobic liquid ends in exactly eight vertical inlets as can be taken from FIG. 1. In another specific embodiment, said first reservoir for uptake of a hydrophobic liquid ends in at least one horizontal inlet. In a more specific embodiment, said first reservoir for uptake of a hydrophobic liquid ends in exactly eight horizontal inlets.

Figure 1:
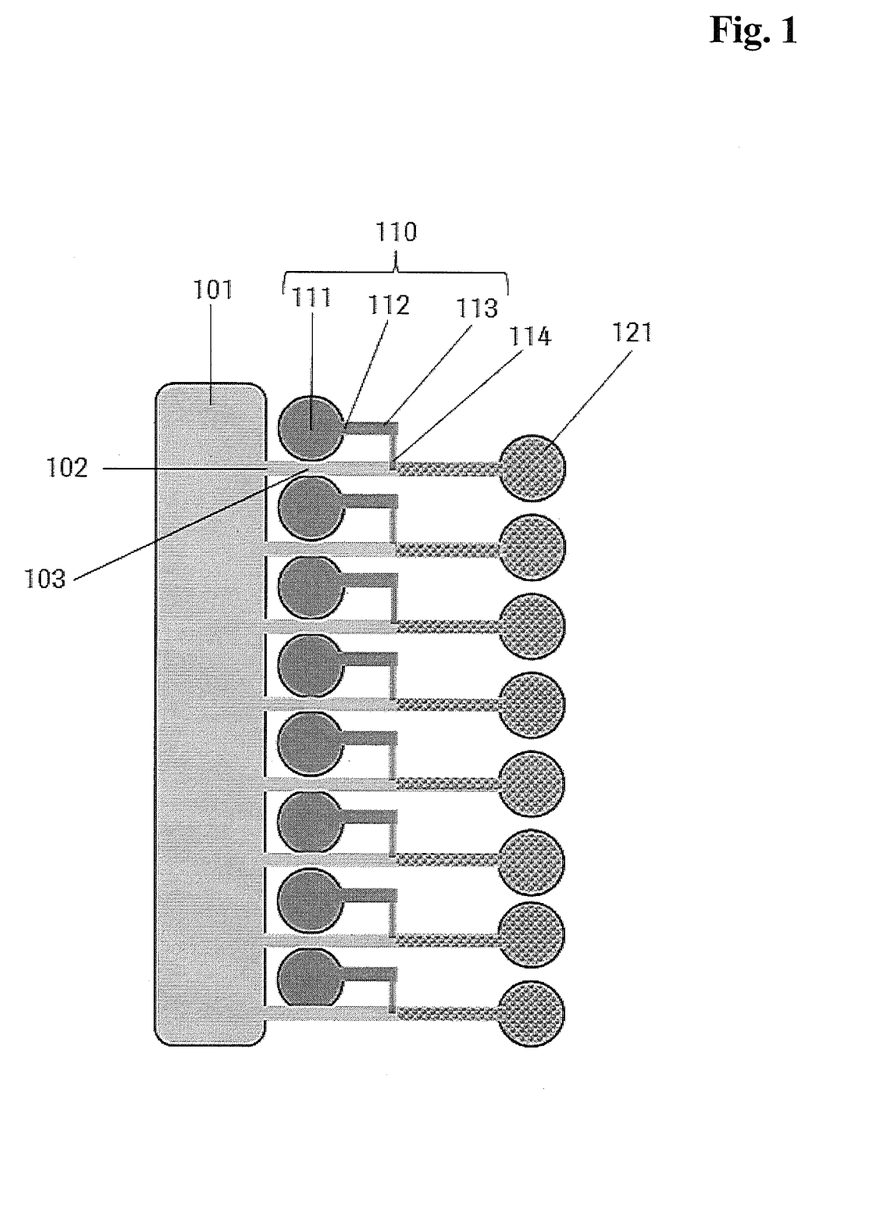
FIG. 1: Shown is microfluidic chip with a first reservoir (101) for uptake of a hydrophobic liquid. The first reservoir (101) comprises at least one inlet (102) connecting the first reservoir (101) with a first microfluidic channel (103). Said first microfluidic channel (103) connecting the at least one first reservoir (101) with a reaction vessel (121). At least one element (110) comprising a second reservoir (111) for uptake of a hydrophilic solution ending in a vertical inlet (112) being the opening into a second microfluidic channel (113). The connection between the first (103) and the second microfluidic channel (113) is designed as a T-junction (114).
Figure 2:
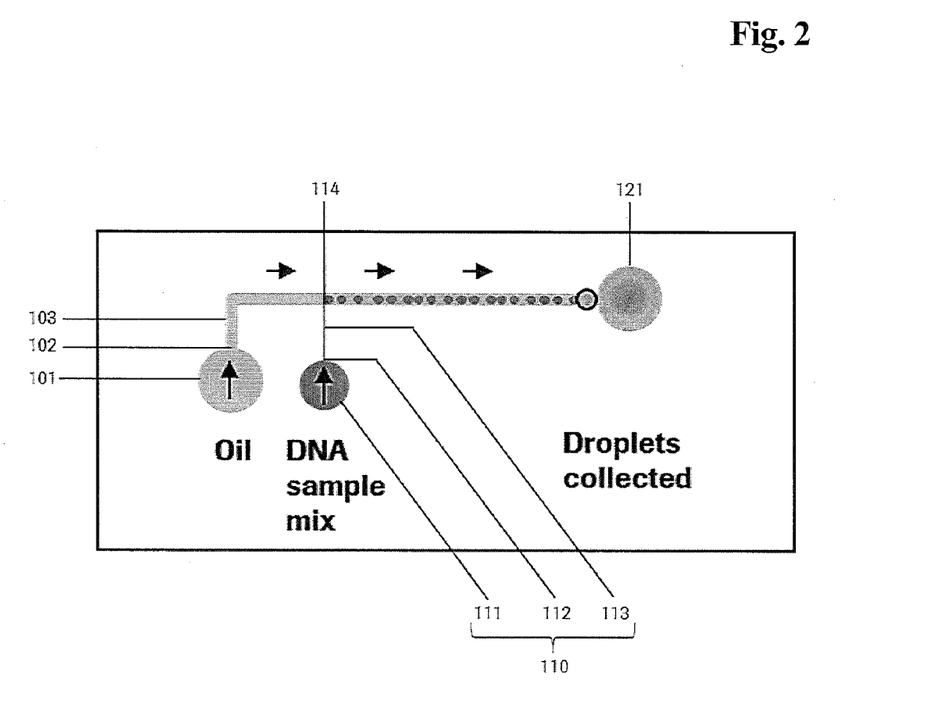
Figure 3:
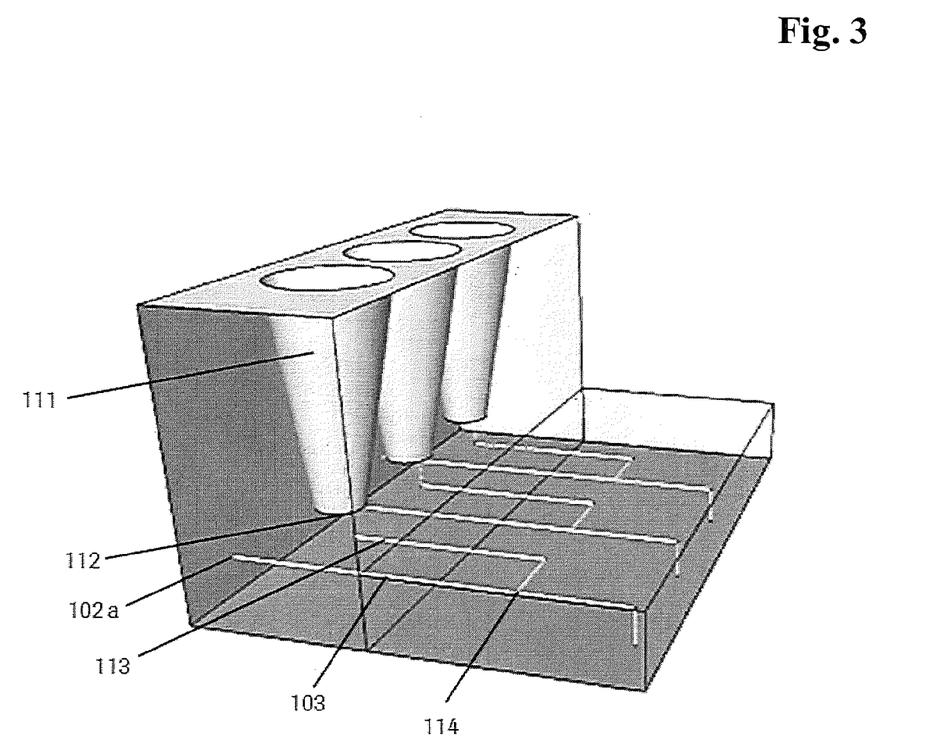
FIG. 3: A three dimensional drawing shows a microfluidic chip with three elements (110), each element comprises a second reservoir (111), a vertical inlet (112) and the second microfluidic channel (113). The second microfluidic channel (113) is connected to the first microfluidic channel (103) via the T-junction (114). In this embodiment, the first reservoir is not located on the microfluidic chip, the hydrophobic liquid is provided through an inlet (102 a) from a reservoir located outside from the microfluidic chip.

In one embodiment, the first reservoir is integral part of the microfluidic chip as shown in FIG. 1. In another embodiment, the first reservoir is not integral part of the microfluidic chip as shown in FIG. 3. In the latter case, the first reservoir is located outside the microfluidic chip and the hydrophobic liquid is transported to the inlet of the first channels of the microfluidic chip by means of tubings.

In one embodiment, one first reservoir ends in exactly one horizontal inlet. In that case, each element comprises additionally one single first reservoir for uptake of a hydrophobic liquid. In a specific embodiment, said first reservoir for uptake of a hydrophobic liquid ends in at least one horizontal inlet. In a more specific embodiment, said first reservoir for uptake of a hydrophobic liquid ends in exactly eight horizontal inlets.

In one embodiment, said first reservoir and said second reservoir is located within the same level. This can be the case if the first reservoir is an integral part of the microfluidic chip. This can also be the case if the first reservoir is not an integral part of the microfluidic chip. In a specific embodiment, said first reservoir is located within a first level and said second reservoir is located within a second level, wherein said first level is located below said second level. This design can be taken from FIG. 3, not showing the first reservoir. This can be the case if the first reservoir is an integral part of the microfluidic chip. This can also be the case if the first reservoir is not an integral part of the microfluidic chip.

In one embodiment, the diameter of said first microfluidic channel is larger than the diameter of said second microfluidic channel. In a specific embodiment the diameter of the first microfluidic channel is between 100 µm and 500 µm. In a more specific embodiment the diameter of the first microfluidic channel is between 200 µm and 400 µm. In an even more specific embodiment the diameter of the first microfluidic channel is 300 µm. In one embodiment the diameter of the second microfluidic channel is between 10 µm and 90 µm. In a more specific embodiment the diameter of the second microfluidic channel is between 25 and 75 µm. In an even more specific embodiment the diameter of the second microfluidic channel is 50 µm.

In a specific embodiment, said T-junction is capable of generating aqueous droplets by means of a continuous flow of hydrophilic solution from the second microfluidic channel into a continuous flow of hydrophobic liquid within the first microfluidic channel. The hydrophilic solution pours out of the second microfluidic channel into the stream of hydrophobic liquid within the first microfluidic channel thereby generating aqueous droplets at the T-junctions. Finally, the aqueous droplet is sheared off the T-junction into the continuous flow of hydrophobic liquid. The moment of shearing off and thus the size of the aqueous droplets depend on the flow rate within the first and the second microfluidic channel, the diameter of the first and the second microfluidic channel and the properties of the hydrophilic solution and the hydrophobic solution.

Figure 4:
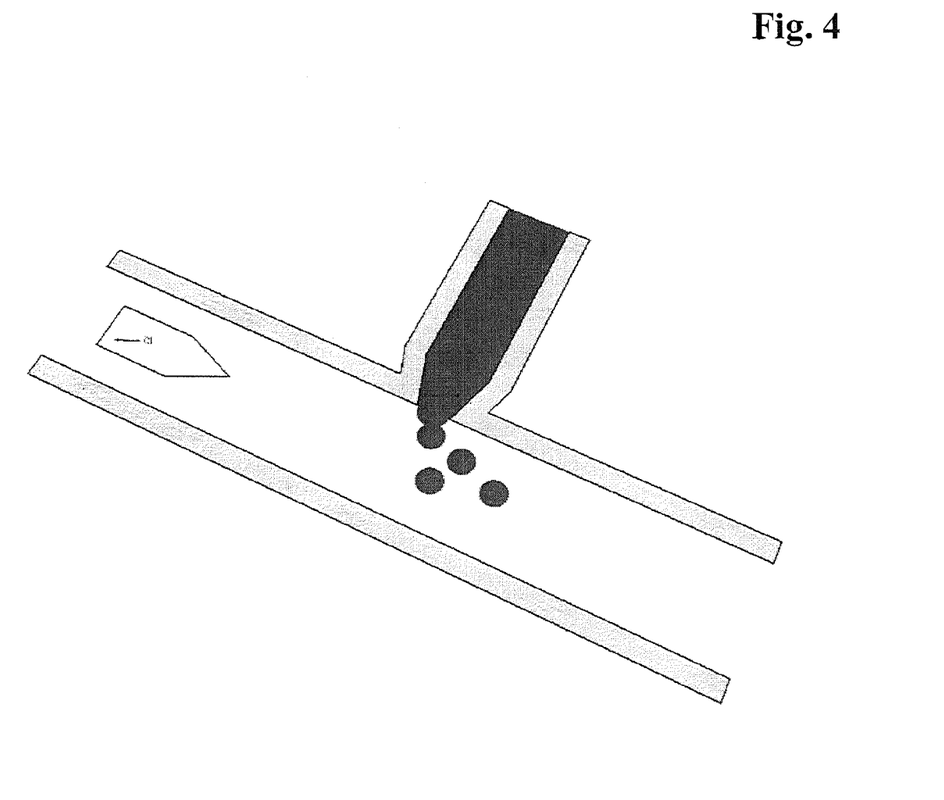
FIG. 4: Shows one embodiment of the T-junction between the first and the second microfluidic channel and the formation of aqueous droplets within the hydrophobic liquid. Only one second microfluidic channel ends into the first microfluidic channel.
Figure 5:
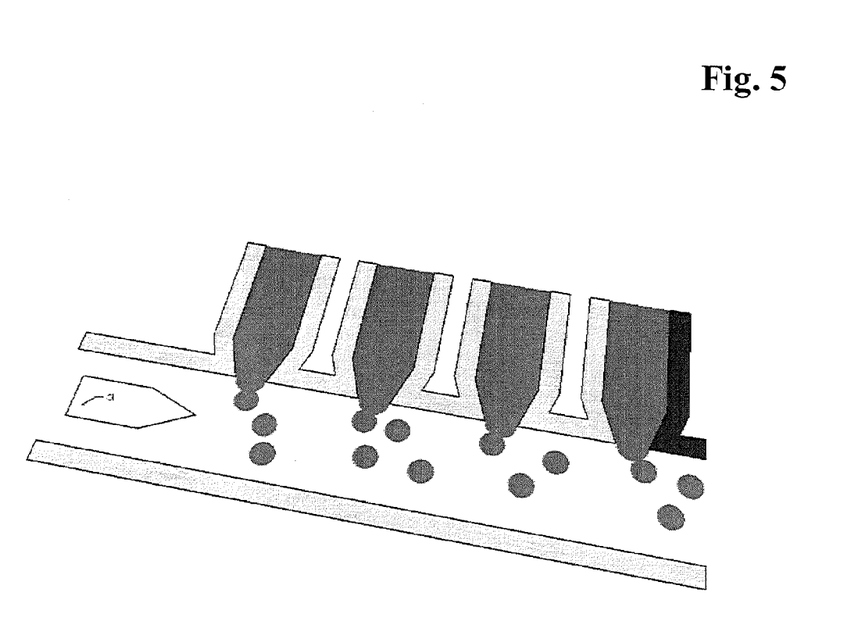
Figure 6:
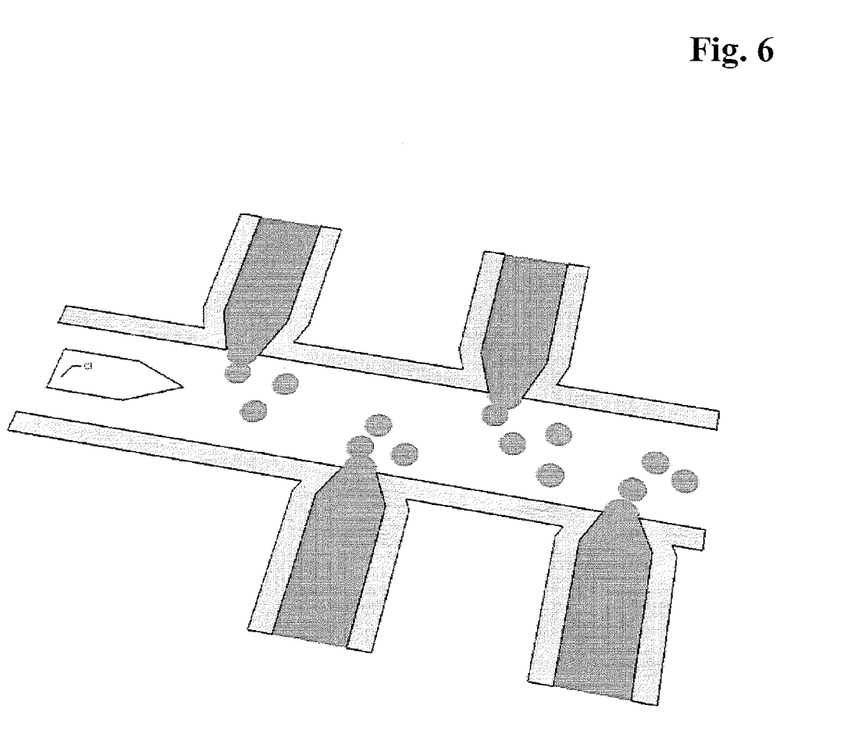
Figure 7:
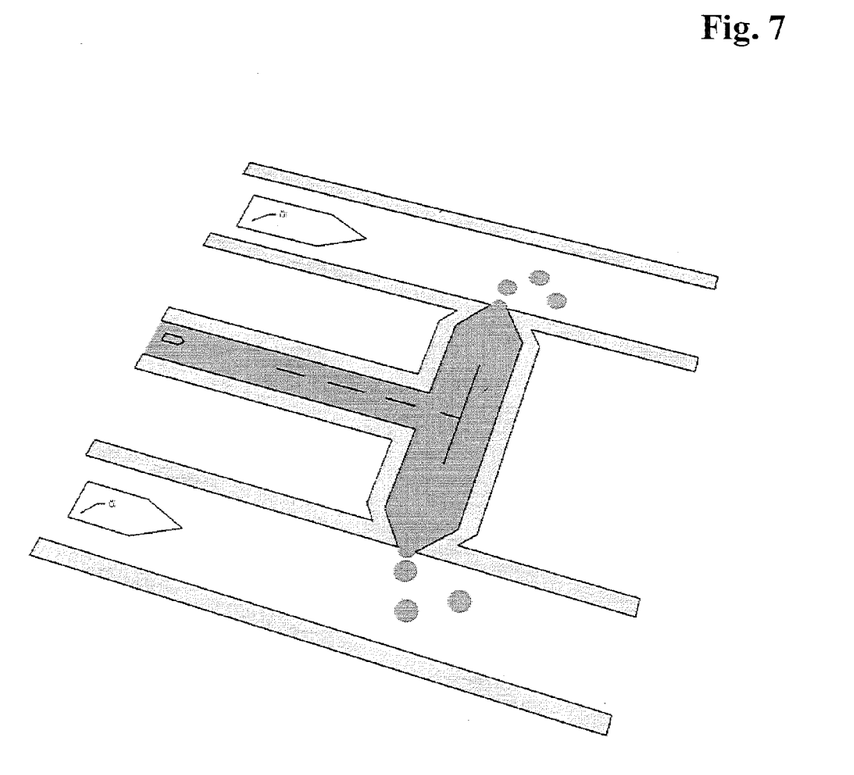
FIG. 7: The figure shows yet another embodiment of the design of the first microfluidic channel carrying the hydrophilic solution for the generation of aqueous droplets. In this case one second microfluidic channel ends in two T-junctions, each of which is connected to one of two first microfluidic channels.
Figure 8:
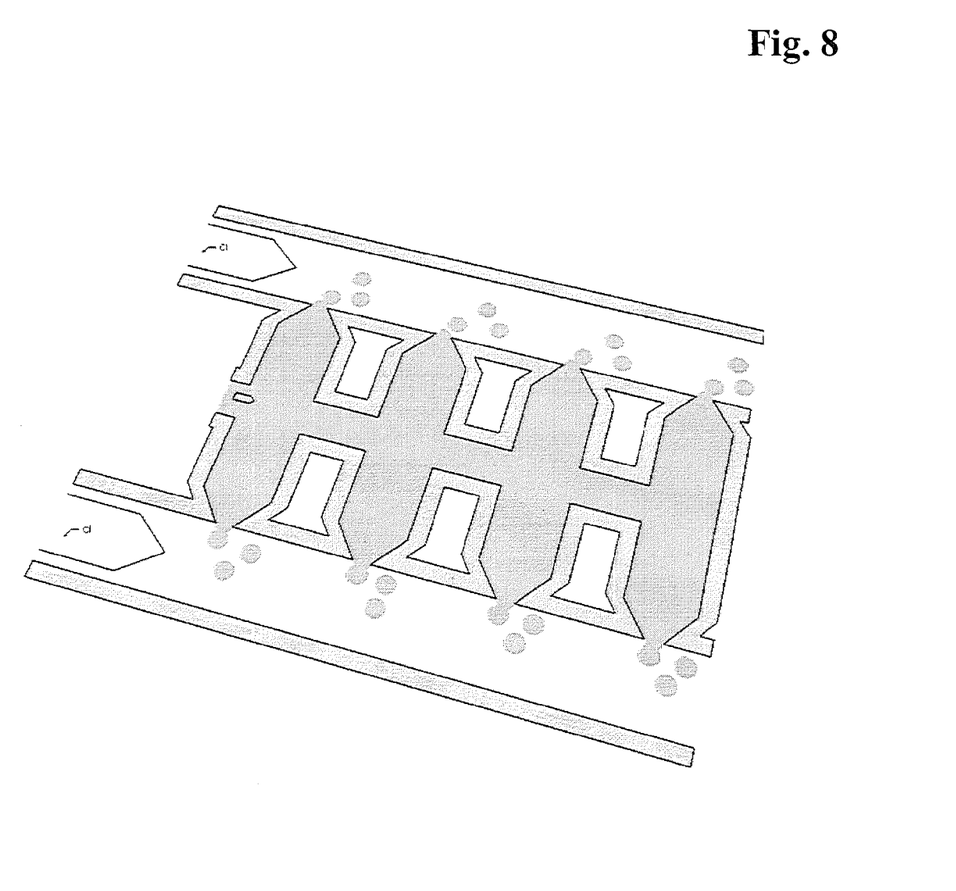
FIG. 8: Shows another embodiment of the design of the structure of the first and the second microfluidic channel for the generation of droplets. In this case one second microfluidic channel ends in eight T-junctions, four of which are connected to one of two first microfluidic channels.

In one embodiment, the T-junction between the first and the second microfluidic channel is designed such that only one second microfluidic channel ends into the first microfluidic channel (FIG. 4). In another embodiment four T-junctions are formed between four endings of the second microfluidic channel and the first microfluidic channel, wherein the four T-junctions are located on the same side of the first microfluidic channel (FIG. 5). In another embodiment four T-junctions are formed between four endings of the second microfluidic channel and the first microfluidic channel, wherein two of the four T-junctions are located on one side of the first microfluidic channel and two of the four T-junctions are located on the other side of the first microfluidic channel (FIG. 6). In one embodiment one second microfluidic channel ends in two T-junctions, wherein each of the two T-junctions is connected to one of two first microfluidic channels (FIG. 7). In one embodiment, one second microfluidic channel ends in eight T-junctions, wherein four of the eight T-junctions are connected to the first of two first microfluidic channels and wherein four of the eight T-junctions are connected to the second of two first microfluidic channels (FIG. 8).

In a specific embodiment, said hydrophilic solution is an aqueous mixture comprising a nucleic acid sample. In a more specific embodiment the hydrophilic solution comprises nucleic acid sample, water, buffer, dNTPs, polymerase, $MgCl_2$, fluorescent labeled probes and primers. In one embodiment, the nucleic acid sample is genomic DNA. In a specific embodiment, the nucleic acid sample is selected from the group consisting of DNA isolated from tissue or single cells, free circulating DNA in plasma or serum, mRNA and miRNA.

In one embodiment, said hydrophobic liquid can comprise any oil. In a specific embodiment, said hydrophobic liquid comprises an emulsion oil or a mixture of emulsion oils. In a more specific embodiment, said hydrophobic liquid comprises an emulsion oil or a mixture of emulsion oils and optionally a surfactant. In a specific embodiment, said emulsion oil is a polysiloxane based oil.

In one embodiment, said microfluidic chip comprises one unit as shown in FIG. 2. In a specific embodiment, said microfluidic chip comprises 48, 32 or 16 units. In a more specific embodiment, said microfluidic chip comprises 8 units. One embodiment of the microfluidic chip comprising 8 elements as shown in FIG. 1, wherein one first reservoir is provided for each of the 8 elements.

In the most specific embodiment, a microfluidic chip is provided for the generation of aqueous droplets for nucleic acid amplification, said microfluidic chip comprising a) one first reservoir for uptake of a polysiloxane oil and a surfactant, the first reservoir ending in eight horizontal inlets, each inlet ending into a first microfluidic channel connecting the first reservoir with a reaction vessel, b) at least one element comprising a second reservoir for uptake of an aqueous mixture comprising a nucleic acid sample, the second reservoir ending in a vertical inlet into a second microfluidic channel connecting the second reservoir with a first microfluidic channel, c) at least one T-junction between said first and second microfluidic channel, characterized in that the end of said second microfluidic channel is joined radial, horizontal and perpendicular to the first microfluidic channel, wherein said T-junction is capable of generating aqueous droplets by means of a continuous flow of hydrophilic solution from the second microfluidic channel into a continuous flow of hydrophobic liquid within the first microfluidic channel, wherein said first reservoir is located within a first level and said second reservoir is located within a second level, wherein said first level is located below said second level, and wherein the diameter of said first microfluidic channel is larger than the diameter of said second microfluidic channel.

The present description is further directed to a device for the generation of aqueous droplets for nucleic acid amplification, the device comprising a microfluidic chip as described above, first means for providing a flow within said first microfluidic channel and second means for providing a flow within said second microfluidic channel.

In one embodiment, said first means is a pressure pump and said second means is a pressure pump. In a specific embodiment the pressure pump is a Mitos P-pump.

In one embodiment, said device further comprises means for holding at least one reaction vessel for collecting the aqueous droplets. In a specific embodiment, said means for holding at least one reaction vessel is a stand for carrying at least one reaction vessel. In a more specific embodiment, said means is capable of holding 16, 32 or 48 reaction vessels. In an even more specific embodiment, said means is capable of holding 8 reaction vessels. In one embodiment, the at least one reaction vessel is selected from the group consisting of a single PCR tube, a PCR strip, and a 96-well plate. In a specific embodiment, the at least one reaction vessel is an 8-well strip. In one embodiment, each of the at least one reaction vessel is capable of receiving a volume of 5 to 100 µL. In a specific embodiment, each of the at least one reaction vessel is capable of receiving a volume of 10 to 50 µL. In a more specific embodiment, each of the at least one reaction vessel is capable of receiving a volume of 20 µL.

In the most specific embodiment, the device for the generation of aqueous droplets for nucleic acid amplification comprises a microfluidic chip as described above, first pressure pump for providing a flow within said first microfluidic channel and second pressure pump for providing a flow within said second microfluidic channel, said device further comprises means for holding 8 reaction vessels, such as an 8-well strip, wherein each reaction vessel is capable of receiving a volume of 20 µL.

The present description is further directed to a system for digital PCR, the system comprising a) a device as described above, b) a thermocycler instrument, and c) a read-out instrument.

In one embodiment, said device, said thermocycler instrument and said read-out instrument are operatively linked to each other.

In one embodiment, the read-out instrument is a flow cytometry instrument. In a specific embodiment, said flow cytometry instrument comprises a laser diode for light generation. In another specific embodiment, said flow cytometry instrument is capable of detecting at least two detection colors. In one embodiment, said read-out instrument is capable of reading 1,000 to 100,000 droplets per second. In a specific embodiment, said read-out instrument is capable of reading 5,000 to 50,000 droplets per second. In a more specific embodiment, said read-out instrument is capable of reading 10,000 droplets per second.

In another embodiment, the said read-out instrument is an imaging instrument. In a specific embodiment, said imaging instrument comprises a monochromatic light source, and either a CCD sensor or a CMOS for detecting the emitted light. In one embodiment, said read-out instrument is capable of reading 1,000 to 100,000 droplets per second. In a specific embodiment, said read-out instrument is capable of reading 5,000 to 50,000 droplets per second. In a more specific embodiment, said read-out instrument is capable of reading 10,000 droplets per second.

In one embodiment, the system comprises at least one reaction vessel capable of collecting aqueous droplets, wherein the transfer of said at least one reaction vessel from the device to the thermocycler instrument can be performed manually or automatically. In a specific embodiment, the automatic transfer can be performed by a robot.

The present description is further directed to the use of the microfluidic chip, device or system as described above for performing digital PCR. In one embodiment, digital PCR is performed for the detection of rare mutations in excess background. In a specific embodiment, the detection of rare mutations in excess background is performed such that 1,000 to 100,000 droplets per second are detected. In a more specific embodiment, the detection of rare mutations in excess background is performed such that 5,000 to 50,000 droplets per second are detected. In an even more specific embodiment, the detection of rare mutations in excess background is performed such that 10,000 droplets per second are detected.

Further, the present description is directed to a method for the generation of aqueous droplets for nucleic acid amplification, the method comprising the steps of a) providing a hydrophobic liquid in a first reservoir, b) providing a hydrophilic solution in a second reservoir, c) generating a first continuous flow of said hydrophobic liquid from said first reservoir through at least one inlet, each inlet ending into a first microfluidic channel, wherein the first microfluidic channel enters into a reaction vessel, d) generating a second continuous flow of said hydrophilic solution from said second reservoir through a second microfluidic channel, wherein the end of said second microfluidic channel is joined to the first microfluidic channel by at least one T-junction, and e) adjusting said first continuous flow and said second contiguous flow such that aqueous droplets of said hydrophilic solution are generated within said first continuous flow of hydrophobic liquid.

In one embodiment, said T-junction is designed such that the end of said second microfluidic channel is joined radial and horizontal to the first microfluidic channel. In a specific embodiment, said T-junction is designed such that the end of said second microfluidic channel is joined perpendicularly to the first microfluidic channel.

In one embodiment, the T-junction between the first and the second microfluidic channel is designed such that only one second microfluidic channel ends into the first microfluidic channel (FIG. 4). In another embodiment four T-junctions are formed between four endings of the second microfluidic channel and the first microfluidic channel, wherein the four T-junctions are located on the same side of the first microfluidic channel (FIG. 5). In another embodiment four T-junctions are formed between four endings of the second microfluidic channel and the first microfluidic channel, wherein two of the four T-junctions are located on one side of the first microfluidic channel and two of the four T-junctions are located on the other side of the first microfluidic channel (FIG. 6). In one embodiment one second microfluidic channel ends in two T-junctions, wherein each of the two T-junctions is connected to one of two first microfluidic channels (FIG. 7). In one embodiment, one second microfluidic channel ends in eight T-junctions, wherein four of the eight T-junctions are connected to the first of two first microfluidic channels and wherein four of the eight T-junctions are connected to the second of two first microfluidic channels (FIG. 8).

In one embodiment, said first continuous flow is generated by a first pressure pump and said second continuous flow is generated by a second pressure pump. In a more specific embodiment, said first pressure pump and said second pressure pump is an external pressure pump. In an even more specific embodiment, said first and said second pressure pump is a Mitos P-Pump.

In a specific embodiment, said hydrophilic solution is an aqueous mixture comprising a nucleic acid sample. In a more specific embodiment the hydrophilic solution comprises nucleic acid sample, water, buffer, dNTPs, polymerase, $MgCl_2$, fluorescent labeled probes and primers. In one embodiment, the nucleic acid sample is genomic DNA. In a specific embodiment, the nucleic acid sample is selected from the group consisting of DNA isolated from tissue or single cells, free circulating DNA in plasma or serum, mRNA and miRNA.

In one embodiment, said hydrophobic liquid can comprise any oil. In a specific embodiment, said hydrophobic liquid comprises an emulsion oil or a mixture of emulsion oils. In a more specific embodiment, said hydrophobic liquid comprises an emulsion oil or a mixture of emulsion oils and optionally a surfactant. In a specific embodiment, said emulsion oil is a polysiloxane based oil.

In one embodiment, the number and size of the aqueous droplets of hydrophilic solution is controlled by means of adjusting the flow rate within said first microfluidic channel and said second microfluidic channel. In a specific embodiment, the flow rate is adjusted such that from 1,000 to 100,000 aqueous droplets are generated within said first microfluidic channel per second. In a more specific embodiment, the flow rate is adjusted such that from 5,000 to 50,000 aqueous droplets are generated within said first microfluidic channel per second. In an even more specific embodiment, the flow rate is adjusted such that 10,000 aqueous droplets are generated within said first microfluidic channel per second.

In another embodiment, the number and size of the aqueous droplets of hydrophilic solution is controlled by adjusting the diameter of said first microfluidic channel in relation to said second microfluidic channel.

In one embodiment, the flow rate in the first and second microfluidic channel is adjusted such that the volume of each aqueous droplet generated within said first microfluidic channel ranges from 5 to 500 pL. In a specific embodiment, the flow rate is adjusted such that the volume of each aqueous droplet generated within said first microfluidic channel ranges from 10 to 50 pL. In a more specific embodiment, the flow rate is adjusted such that the volume of each aqueous droplet generated within said first microfluidic channel ranges is 20 pL.

In one embodiment, the flow rate in the first and second microfluidic channel is adjusted such that the diameter of each aqueous droplet generated within said first microfluidic channel ranges from 10 to 100 µm. In a specific embodiment, the flow rate is adjusted such that the diameter of each aqueous droplet generated within said first microfluidic channel ranges from 20 to 50 µm. In a more specific embodiment, the flow rate is adjusted such that the diameter of each aqueous droplet generated within said first microfluidic channel ranges from 30 to 40 µm.

In one embodiment, said hydrophilic solution is an aqueous mixture comprising the nucleic acid sample, wherein the concentration of nucleic acids within said sample is adjusted to provide at average one nucleic acid molecule per droplet. In a specific embodiment, the concentration of nucleic acids within said sample is adjusted to one sequence copy in 1 to 100 pL. In a more specific embodiment, the concentration of nucleic acids within said sample is adjusted to one sequence copy in 4 to 70 pL. In a more specific embodiment, the concentration of nucleic acids within said sample is adjusted to one sequence copy in 10 to 50 pL. In an even more specific embodiment, the concentration of nucleic acids within said sample is adjusted to one sequence copy in 14 to 34 pL.

In one embodiment, said aqueous droplets generated within said first microfluidic channel are collected within the reaction vessel. In a specific embodiment, the reaction vessel is selected from the group consisting of a single PCR tube, a PCR strip, and a 96-well plate. In a more specific embodiment, the reaction vessel is an 8-well strip.

In one embodiment, the volume collected in a reaction vessel is 10 to 100 µL. In a specific embodiment, the volume collected in a reaction vessel is 5 to 50 µL. In a more specific embodiment, the volume collected in a reaction vessel is 20 µL.

In one embodiment, 1,000 to 100,000 droplets are detected per second. In a specific embodiment, 5,000 to 50,000 droplets are detected per second. In a more specific embodiment, 10,000 droplets are detected per second.

In the most specific embodiment, provided is a method for the generation of aqueous droplets for nucleic acid amplification, the method comprising the steps of a) providing a polysiloxane based oil in a first reservoir, b) providing an aqueous mixture comprising a nucleic acid sample in a second reservoir, c) generating by a first pressure pump a first continuous flow of said polysiloxane based oil from said first reservoir through eight horizontal inlets, each inlet ending into a first microfluidic channel, wherein the first microfluidic channel enters into a reaction vessel, d) generating by a second pressure pump a second continuous flow of said aqueous mixture from said second reservoir through a second microfluidic channel, wherein the end of said second microfluidic channel is joined perpendicular to the first microfluidic channel by at least one T-junction, and e) adjusting said first continuous flow and said second contiguous flow such that aqueous droplets of said aqueous mixture are generated within said first continuous flow of said polysiloxane based oil, wherein said first reservoir is located within a first level and said second reservoir is located within a second level, wherein said first level is located below said second level, and wherein the diameter of said first microfluidic channel is larger than the diameter of said second microfluidic channel, wherein said T-junction is capable of generating aqueous droplets by means of a continuous flow of aqueous mixture from the second microfluidic channel into a continuous flow of polysiloxane based oil within the first microfluidic channel, and wherein the size of the aqueous droplets is dependent from the ratio of the flow rate within and the dimensions of the first microfluidic channel and the second microfluidic channel.

The description is further directed to a method for the generation of aqueous droplets in emulsion oil for nucleic acid amplification using a microfluidic chip, device or system as described above. In a specific embodiment, the method is performed as described above.

Further embodiments are included by the following items:

1. A microfluidic chip for the generation of aqueous droplets for nucleic acid amplification, said microfluidic chip comprising a) a first reservoir for uptake of a hydrophobic liquid ending in at least one inlet or at least one inlet coming from an external reservoir of hydrophobic liquid, each inlet ending into a first microfluidic channel connecting the at least one first reservoir with a reaction vessel, b) at least one element comprising a second reservoir for uptake of a hydrophilic solution ending in a vertical inlet into a second microfluidic channel connecting the second reservoir with a first microfluidic channel, c) at least one T-junction between said first and second microfluidic channel, characterized in that the end of said second microfluidic channel is joined radial and horizontal to the first microfluidic channel.

2. The microfluidic chip of item 1, wherein said end of the second channel is joined to the first channel perpendicularly.

3. The microfluidic chip of items 1 or 2, wherein said first reservoir for uptake of a hydrophobic liquid ends in at least one vertical inlet.

4. The microfluidic chip of items 1 or 2, wherein said first reservoir for uptake of a hydrophobic liquid ends in at least one horizontal inlet.

5. The microfluidic chip of item 4, wherein said first reservoir is located within a first level and said second reservoir is located within a second level, wherein said first level is located below said second level.

6. The microfluidic chip of items 1 to 5, wherein the diameter of said first microfluidic channel is larger than the diameter of said second microfluidic channel.

7. The microfluidic chip of items 1 to 6, wherein said T-junction is capable of generating aqueous droplets by means of a continuous flow of hydrophilic solution from the second microfluidic channel into a continuous flow of hydrophobic liquid within the first microfluidic channel.

8. The microfluidic chip of items 1 to 7, wherein the size of the aqueous droplets is dependent from the ratio of the flow rate within and the dimensions of the first microfluidic channel and the second microfluidic channel.

9. The microfluidic chip of items 1 to 8, wherein said hydrophilic solution is an aqueous mixture comprising a nucleic acid sample.

10. The microfluidic chip of items 1 to 9, wherein said hydrophobic liquid comprises an emulsion oil or a mixture of emulsion oils and optionally a surfactant.

11. The microfluidic chip of item 10, wherein said emulsion oil is a polysiloxane based oil.

12. The microfluidic chip of items 1 to 11, wherein the microfluidic chip comprises 8, 16, 32 or 48 elements.

13. A device for the generation of aqueous droplets for nucleic acid amplification, the device comprising a microfluidic chip according to items 1 to 12, first means for providing a flow within said first microfluidic channel and second means for providing a flow within said second microfluidic channel.

14. The device of item 13, wherein said first means is a pressure pump and said second means is a pressure pump.

15. The device of items 13 or 14 further comprising means for holding at least one reaction vessel for collecting the aqueous droplets.

16. The device of items 13 to 15, wherein the at least one reaction vessel is selected from the group consisting of a single PCR tube, a PCR strip, for example an 8-well strip, and a 96-well plate.

17. The device of items 13 to 16, wherein each of the at least one reaction vessel is capable of receiving a volume of 5 to 100 µL, for example 10 to 50 µL and 20 µL.

18. A system for digital PCR, the system comprising d) a device according to items 13 to 17, e) a thermocycler instrument, and
f) a read-out instrument.

19. The system of item 18, wherein said device, said thermocycler instrument and said read-out instrument are operatively linked to each other.

20. The system of items 18 or 19, wherein said read-out instrument is a flow cytometry instrument.

21. The system of item 20, wherein said flow cytometry instrument comprises a laser diode for light generation.

22. The system of items 20 or 21, wherein said flow cytometry instrument is capable of detecting at least two detection colors.

23. The system of items 18 or 19, wherein said read-out instrument is an imaging instrument.

24. The system of item 23, wherein said imaging instrument comprises a monochromatic light source, and either a CCD sensor or a CMOS for detecting the emitted light.

25. The system of items 18 to 24, wherein said read-out instrument is capable of reading 1,000 to 100,000 droplets per second, for example 5,000 to 50,000 droplets per second or 10,000 droplets per second.

26. The system of items 18 to 25, wherein the system comprises at least one reaction vessel capable of collecting aqueous droplets, wherein the transfer of said at least one reaction vessel from the device to the thermocycler instrument can be performed manually or automatically.

27. Use of the microfluidic chip, device or system according to items 1 to 26 for performing digital PCR.

28. The use of item 27, wherein digital PCR is performed for the detection of rare mutations in excess background.

29. The use of items 27 or 28, wherein the detection of rare mutations in excess background is performed such that 1,000 to 100,000 droplets per second are detected, for example 5,000 to 50,000 droplets per second and 10,000 droplets per second.

30. A method for the generation of aqueous droplets for nucleic acid amplification, the method comprising the steps of
   g) providing a hydrophobic liquid in a first reservoir,
   h) providing a hydrophilic solution in a second reservoir
   i) generating a first continuous flow of said hydrophobic liquid from said first reservoir through at least one inlet, each inlet ending into a first microfluidic channel, wherein the first microfluidic channel enters into a reaction vessel,
   j) generating a second continuous flow of said hydrophilic solution from said second reservoir through a second microfluidic channel, wherein the end of said second microfluidic channel is joined to the first microfluidic channel by at least one T-junction, and
   k) adjusting said first continuous flow and said second contiguous flow such that aqueous droplets of said hydrophilic solution are generated within said first continuous flow of hydrophobic liquid.

31. The method of item 30, wherein said T-junction is designed such that the end of said second microfluidic channel is joined radial and horizontal to the first microfluidic channel, for example perpendicularly.

32. The method of item 31, wherein said first continuous flow is generated by a first pressure pump and said second continuous flow is generated by a second pressure pump.

33. The method of item 32, wherein said first pressure pump and said second pressure pump is an external pressure pump.

34. The method of items 30 to 33, wherein said hydrophilic solution is an aqueous mixture comprising a nucleic acid sample.

35. The method of items 30 to 34, wherein said hydrophobic liquid comprises an emulsion oil or a mixture of emulsion oils and optionally a surfactant.

36. The method of item 35, wherein said emulsion oil is a polysiloxane based oil.

37. The method of items 30 to 36, wherein the number and size of the aqueous droplets of hydrophilic solution is controlled by means of adjusting the flow rate within said first microfluidic channel and said second microfluidic channel.

38. The method of item 37, wherein the flow rate is adjusted such that from 1,000 to 100,000 aqueous droplets are generated within said first microfluidic channel per second, for example 5,000 to 50,000 aqueous droplets per second and 10,000 aqueous droplets per second.

39. The method of items 37 or 38, wherein the flow rate is adjusted such that the volume of each aqueous droplet generated within said first microfluidic channel ranges from 5 to 500 pL, for example 10 to 50 pL and each aqueous droplet has a volume of about 20 pL.

40. The method of items 37 to 39, wherein the flow rate is adjusted such that the diameter of each aqueous droplet generated within said first microfluidic channel ranges from 10 to 100 µm, for example 20 to 50 µm or 30 to 40 µm.

41. The method of items 30 to 40, wherein said hydrophilic solution is an aqueous mixture comprising the nucleic acid sample, wherein the concentration of nucleic acids within said sample is adjusted to provide at average one nucleic acid molecule per droplet.

42. The method of items 30 to 41, wherein the aqueous droplets generated within said first microfluidic channel are collected within the reaction vessel.

43. The method of items 30 to 42, wherein the reaction vessel is selected from the group consisting of a single PCR tube, a PCR strip, for example an 8-well strip, and a 96-well plate.

44. The method of items 30 to 43, wherein the volume collected in a reaction vessel is 10 to 100 µL, for example 5 to 50 µL and 20 µL.

45. The method of items 30 to 44, wherein 1,000 to 100,000 droplets are detected per second, for example 5,000 to 50,000 droplets per second or 10,000 droplets per second.

46. A method for the generation of aqueous droplets in emulsion oil for nucleic acid amplification using a microfluidic chip, device or system according to items 1 to 26.

47. The method of item 46, wherein the method is performed according to items 30 to 45.

While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A microfluidic chip for the generation of aqueous droplets for nucleic acid amplification, said microfluidic chip comprising:
   (a) a first reservoir for uptake of a hydrophobic liquid ending in a plurality of inlets, wherein each inlet of said plurality of inlets is fluidly connected to one of a plurality of reaction vessels via one of a plurality of first microfluidic channels, wherein each inlet of said plurality of inlets is fluidly connected to a different first microfluidic channel of said plurality of first microfluidic channels, and each different first microfluidic channel is connected to a different reaction vessel, and (b) a plurality of second reservoirs for uptake of a hydrophilic solution, wherein each second reservoir of said plurality of second reservoirs ends in a vertical inlet fluidly connected to one of a plurality of second microfluidic channels connecting each second reservoir with a different first microfluidic channel via at least one T-junction, wherein said first reservoir is located within a first level and each second reservoir is located within a second level, wherein said first level is located below said second level, and wherein said at least one T-junction is characterized in that the end of each second microfluidic channel is joined to a different first microfluidic channel perpendicularly.

2. The microfluidic chip of claim 1, comprising said hydrophilic solution and said hydrophobic liquid, wherein said hydrophilic solution is an aqueous mixture comprising a nucleic acid sample and wherein said hydrophobic liquid comprises an emulsion oil or a mixture of emulsion oils and optionally a surfactant.

3. A device for the generation of aqueous droplets for nucleic acid amplification, the device comprising a microfluidic chip according to claim 1, wherein flow within each of said plurality of first and second microfluidic channels is provided by at least one pressure pump.

4. The device of claim 3 further comprising a stand configured to hold at least one reaction vessel for collecting the aqueous droplets, wherein the at least one reaction vessel is selected from the group consisting of a single PCR tube, a PCR strip or a 96-well plate.

5. The microfluidic chip of claim 4, wherein the at least one reaction vessel is an 8-well strip.

6. A system for digital PCR, the system comprising:
(a) a device according to claim 3,
(b) a thermocycler instrument, and
(c) a read-out instrument, wherein said thermocycler instrument and said read-out instrument are operatively linked to each other.

7. The system of claim 6, wherein said read-out instrument is a flow cytometry instrument or an imaging instrument.

8. The system of claim 6, wherein said read-out instrument is capable of reading 1,000-100,000 droplets per second.

9. A method for the generation of aqueous droplets for nucleic acid amplification in a device comprising a microfluidic chip according to claim 1, the method comprising the steps of:
(a) providing a hydrophobic liquid in said first reservoir,
(b) providing a hydrophilic solution in at least one second reservoir,
(c) generating a first continuous flow of said hydrophobic liquid from said first reservoir through at least one inlet of said plurality of inlets,
(d) generating a second continuous flow of said hydrophilic solution from said second reservoir through a second microfluidic channel of said plurality of second microfluidic channels, and
(e) adjusting said first continuous flow and said second continuous flow such that aqueous droplets of said hydrophilic solution are generated within said first continuous flow of hydrophobic liquid.

10. The method of claim 9, wherein said hydrophilic solution is an aqueous mixture comprising a nucleic acid sample and said hydrophobic liquid comprises an emulsion oil or a mixture of emulsion oils and optionally a surfactant.

11. The method of claim 9, wherein the reaction vessel is selected from the group consisting of a single PCR tube or a PCR strip.

12. A method for the generation of aqueous droplets in emulsion oil for nucleic acid amplification using the device of claim 3 or the system of claim 6, the method comprising the steps of:
(a) providing a hydrophobic liquid in said first reservoir,
(b) providing a hydrophilic solution in at least one second reservoir,
(c) generating a first continuous flow of said hydrophobic liquid from said first reservoir through at least one inlet of said plurality of inlets,
(d) generating a second continuous flow of said hydrophilic solution from said second reservoir through a second microfluidic channel of said plurality of second microfluidic channels, and
(e) adjusting said first continuous flow and said second continuous flow such that aqueous droplets of said hydrophilic solution are generated within said first continuous flow of hydrophobic liquid.

* * * * *